(12) United States Patent
Smith et al.

(10) Patent No.: US 10,031,040 B1
(45) Date of Patent: Jul. 24, 2018

(54) METHOD AND SYSTEM FOR ANALYZING GAS LEAK BASED ON MACHINE LEARNING

(71) Applicant: Palo Alto Research Center Incorporated, Palo Alto, CA (US)

(72) Inventors: Clinton J. Smith, San Francisco, CA (US); Bhaskar Saha, Redwood City, CA (US); Victor A. Beck, Milpitas, CA (US); David E. Schwartz, San Carlos, CA (US)

(73) Assignee: PALO ALTO RESEARCH CENTER INCORPORATED, Palo Alto, CA (US)

( * ) Notice: Subject to any disclaimer, the term of this patent is extended or adjusted under 35 U.S.C. 154(b) by 0 days.

(21) Appl. No.: 15/472,018

(22) Filed: Mar. 28, 2017

(51) Int. Cl.
*G06K 9/00* (2006.01)
*G01M 3/00* (2006.01)
*G01B 11/28* (2006.01)
*G06T 7/514* (2017.01)
*G06T 5/00* (2006.01)
*G06T 7/557* (2017.01)
*G06T 7/00* (2017.01)

(52) U.S. Cl.
CPC ............ *G01M 3/007* (2013.01); *G01B 11/28* (2013.01); *G06T 5/003* (2013.01); *G06T 7/001* (2013.01); *G06T 7/514* (2017.01); *G06T 7/557* (2017.01); *G06T 2207/10004* (2013.01); *G06T 2207/10024* (2013.01); *G06T 2207/20081* (2013.01); *G06T 2207/30204* (2013.01)

(58) Field of Classification Search
CPC ......... G01M 3/007; G01M 3/38; G06T 7/514; G06T 7/557; G06T 5/003; G06T 7/001; G06T 2207/10024; G06T 2207/20081; G06T 2207/30204; G01B 11/28; G06K 9/00201
USPC ........................................................ 382/154
See application file for complete search history.

(56) References Cited

U.S. PATENT DOCUMENTS

| 2017/0097274 A1* | 4/2017 | Thorpe | G01B 21/20 |
| 2017/0097302 A1* | 4/2017 | Kreitinger | G01B 21/20 |
| 2017/0284891 A1* | 10/2017 | Miranda | G01M 3/16 |
| 2017/0336281 A1* | 11/2017 | Waxman | G01M 3/38 |

* cited by examiner

*Primary Examiner* — Daniel Mariam
(74) *Attorney, Agent, or Firm* — Shun Yao; Park, Vaughan, Fleming & Dowler LLP

(57) ABSTRACT

Embodiments of the present invention provide a system for estimating a location of a gas leak, based on machine learning from forward gas concentration data provided by an analog or scale model including a gas source. The system improves significantly over previous systems by providing high quality, physically accurate forward modeling data inexpensively. During operation, the system configures an aerosol source at a first location to emit a gaseous aerosol. The system then configures a laser source to illuminate the aerosol with a laser sheet. The system may then obtain an image of a reflection of the laser sheet from the aerosol. The system may then analyze the image to quantify a three-dimensional concentration distribution of the aerosol. The system may then estimate, based on solving an inverse problem and an observed second gas concentration, a second location of a second gas source.

20 Claims, 9 Drawing Sheets

SYSTEM 200

Figure 1:
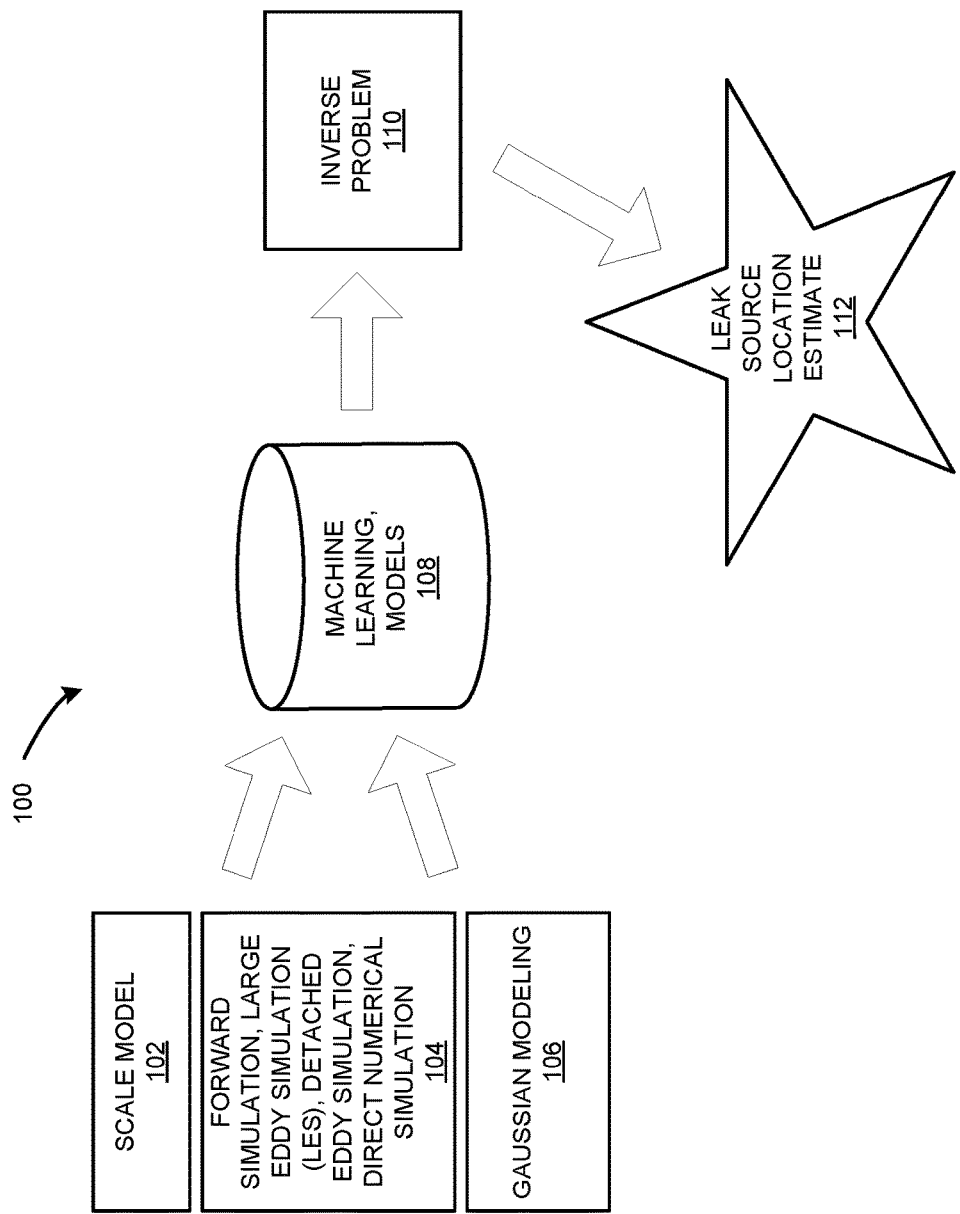

- 206
- 210A, 210B, 210C, 210D, 210E, 210F, 210G, 210H
- STORAGE DEVICE 204
- GAS CONCENTRATION MEASUREMENT MODULE 202
- IMAGES AND MODELS 208
- LASER 212
- CAMERA 214
- AEROSOL SOURCE 216

FIG. 2

```
                              ┌─ 400
        START

↓
CONFIGURE AN AEROSOL SOURCE AT A FIRST LOCATION TO EMIT A GASEOUS
AEROSOL
402

↓
CONFIGURE A LASER SOURCE TO ILLUMINATE THE GASEOUS AEROSOL WITH
A LASER SHEET
404

↓
OBTAIN, FROM A CAMERA, AN IMAGE OF A REFLECTION OF THE LASER SHEET
FROM A PLURALITY OF PARTICLES OF THE GASEOUS AEROSOL
406

↓
ANALYZE THE IMAGE TO QUANTIFY A THREE-DIMENSIONAL CONCENTRATION
DISTRIBUTION OF THE GASEOUS AEROSOL ASSOCIATED WITH THE FIRST
LOCATION
408

↓
SOLVE AN INVERSE PROBLEM BASED ON THE THREE-DIMENSIONAL
CONCENTRATION DISTRIBUTION AND THE FIRST LOCATION
410

↓
ESTIMATE A SECOND LOCATION OF A SECOND GAS SOURCE BASED ON THE
SOLVED INVERSE PROBLEM AND AN OBSERVED SECOND GAS
CONCENTRATION
412

↓
         END
```

FIG. 4

METHOD AND SYSTEM FOR ANALYZING GAS LEAK BASED ON MACHINE LEARNING

STATEMENT OF GOVERNMENT-FUNDED RESEARCH

This invention was made with U.S. government support under Contract No. DE-AR0000542 awarded by the Advanced Research Projects Agency in the Department of Energy (ARPA-E). The U.S. government has certain rights in this invention.

BACKGROUND

Field

The present disclosure relates to measuring a gas concentration distribution. More specifically, this disclosure relates to a method and system for estimating a location of a gas leak, based on machine learning from forward data provided by an analog or scale model including a gas source.

Related Art

Natural gas or other gas leaks are an important economic and environmental problem. A recent federal study estimated that the financial cost of natural gas lost to leaks, in Massachusetts alone, reached $1.5 billion from 2000 to 2011. Gas leaks are extremely dangerous, posing fire and explosion hazards, and in some cases may necessitate emergency responses. Natural gas is also a very powerful greenhouse gas, therefore gas leaks significantly contribute to greenhouse gas emission. Moreover, leaks can cause harm to flora and fauna. In order to prevent and mitigate such economic costs, health and safety hazards, and environmental damage due to gas leaks, it is crucial for qualified personnel to be able to locate the leaks quickly and accurately.

Current methods for localizing gas leaks typically use Gaussian plume models to model the dispersion of the leak. Such Gaussian dispersion models are frequently used by mobile gas analyzers equipped on vehicles or aircraft to locate leaks, with a resolution of hundreds of meters to kilometers. The Gaussian models have the advantage of being easily invertible, in order to convert analyzer sensor data into a reconstruction of a plume's orientation, source, and corresponding leak rate.

But unfortunately, turbulent and chaotic effects, which are neglected by such models, are important for the detailed study of gas and aerosol dispersion in wind. Specifically, because gas leaks usually originate from well-pads or other equipment near ground level, ground roughness, bluff bodies, etc., can contribute to turbulent flow conditions. Therefore, Gaussian techniques are limited to leak resolution over scales of at least hundreds of meters—i.e., these techniques are valid in the "far field," many characteristic lengths, or dimensions of surrounding bluff bodies, from the leak source. Over these larger distances, the chaotic effects of turbulent flow are small in comparison to the overall plume shape and direction and eventually become averaged out.

Such large-scale location of leaks is valuable to determine whether a particular oil/gas site is emitting pollution, yet Gaussian methods are incapable of singling out a specific well-pad component, or set of components, as the likely source of a leak. Thus from an operator's perspective, systems measuring from a distance using inverted Gaussian dispersion models fail to provide relevant intelligence for locating and fixing leak sources.

In order to provide such actionable data, a more precise, yet costly, solution is to invert numerical gas leak simulations (based, for example, on the Navier-Stokes equation) that are powerful enough to take into account turbulent flow. High-quality forward numerical simulations (i.e., simulations of gas concentration as a function of the leak location and wind and terrain conditions) could then be inverted to provide precise leak localization given an observed gas distribution. One way to accomplish this inversion is to use the forward simulations as training data for machine learning algorithms to solve the inverse problem, i.e. leak localization as a function of the observed distribution and wind and terrain conditions.

But sufficiently accurate forward simulation of realistic environmental conditions is highly nonlinear, and is a computationally and theoretically intensive task. Although several Reynold's Stress Models may be applied to forward modeling of turbulent flows (e.g., k-$\varepsilon$, k-$\omega$, etc.), these only apply in steady-state conditions. When modeling the time-dependent concentration of a diffusive species in a turbulent flow field, these steady-state models are not applicable.

On the other hand, non-steady computational models (such as Large Eddy Simulation, Detached Eddy Simulation, Direct Numerical Simulation, etc.), are very resource-intensive. This is because current state-of-the-art incompressible flow models employ finite-element methods, the accuracy of which depend on the mesh resolution. This challenge may be compounded by the fact that turbulent and chaotic flow conditions are particularly sensitive to numerical error, and therefore to the mesh resolution. Non-steady numerical simulation would thus require considerable effort to apply to a specific environment and attain acceptable accuracy and realism. As a result, in the case of a typical well-pad, over 100,000 cubic meters of volume must be numerically simulated with a centimeter-resolution mesh. Even with adaptive or fractal grids, such a task would currently require supercomputer-level computing power and a significant amount of computing time.

SUMMARY

One embodiment of the present invention provides a system and method for measuring a gas concentration distribution. During operation, the system configures an aerosol source at a first location to emit a gaseous aerosol. The system then configures a laser source to illuminate the gaseous aerosol with a laser sheet. The system may then obtain, from a camera, an image of a reflection of the laser sheet from a plurality of particles of the gaseous aerosol. The system may then analyze the image to quantify a three-dimensional concentration distribution of the gaseous aerosol associated with the first location. The system may then solve, based on the three-dimensional concentration distribution and the first location, an inverse problem. The system may then estimate, based on the solved inverse problem and an observed second gas concentration, a second location of a second gas source.

In a variation on this embodiment, the first location of the aerosol source may be within a wind tunnel or a turbulent wind tunnel.

In a variation on this embodiment, the system may select a relative wind direction by configuring a turn table to rotate the aerosol source within the wind tunnel or turbulent wind tunnel.

In a variation on this embodiment, configuring the aerosol source at the first location involves selecting the aerosol source from a set of multiple sources located at predetermined locations.

In a variation on this embodiment, the system may configure the laser source to illuminate the gaseous aerosol with a plurality of laser sheets at different heights and/or orientations. The system may then obtain, from the camera, a plurality of images of reflections of the plurality of laser sheets from the gaseous aerosol. The system may then analyze the plurality of images to quantify the three-dimensional concentration distribution of the gaseous aerosol.

In a variation on this embodiment, analyzing the image involves one or more of: correcting for a placement of the camera by a perspective transformation; calibrating a spatial scale of the image using a set of fiduciary points at known fiduciary locations; removing artifacts from the image by differencing an artifact image, wherein the artifact image is taken with the aerosol source configured not to emit the gaseous aerosol; suppressing an aerosol signature originating out of a plane of the laser sheet by correlating a set of red, green, and blue (RGB) values for a respective pixel within the image; and isolating a plume of the gaseous aerosol within the image by analyzing connectedness of shapes in the image.

In a variation on this embodiment, the first location of the aerosol source may be in a scale model of a well-pad, and the second gas source may be a natural gas leak.

BRIEF DESCRIPTION OF THE FIGURES

FIG. 1 illustrates an exemplary overall process flow for estimating a location of a gas leak, according to embodiments of the present invention.

FIG. 2 presents a block diagram illustrating an exemplary gas source location estimating system utilizing the gas concentration measurement method, according to embodiments of the present invention.

FIG. 3 illustrates an exemplary gas concentration measurement setup, according to embodiments of the present invention.

FIG. 4 presents a block diagram illustrating a method for measuring a gas concentration distribution, according to embodiments of the present invention.

FIG. 5A illustrates an exemplary gaseous aerosol concentration image analyzed by background removal, in accordance with embodiments of the present invention.

FIG. 5B illustrates exemplary fiduciary points used to correct perspective, in accordance with embodiments of the present invention.

FIG. 5C illustrates an exemplary gaseous aerosol concentration image analyzed by background removal and perspective correction, in accordance with embodiments of the present invention.

FIG. 6 illustrates an exemplary heat map showing gaseous aerosol plume intensity, in accordance with embodiments of the present invention.

FIG. 7 presents a block diagram illustrating an exemplary apparatus for gas concentration measurement, in accordance with embodiments of the present invention.

FIG. 8 presents a block diagram illustrating an exemplary computer system for gas concentration measurement, in accordance with embodiments of the present invention.

In the figures, like reference numerals refer to the same figure elements.

DETAILED DESCRIPTION

The following description is presented to enable any person skilled in the art to make and use the embodiments, and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present invention is not limited to the embodiments shown, but is to be accorded the widest scope consistent with the principles and features disclosed herein.

Overview

Embodiments of the present invention solve the problem of estimating a location of a gas leak precisely, by providing forward gas concentration data from an analog or physical scale model including a gas source. The system can use image processing to determine and analyze the gas concentration from images of the scale model, even without carrying out numerical simulation. Consequently, the system provides high-quality forward modeling of the gas concentration (i.e., determines concentration as a function of the leak location and wind and terrain conditions) based on the scale model, with guaranteed physical accuracy. Moreover, the system can train machine learning models to invert this forward modeling data, providing precise gas leak localization and/or leak flux quantification, from a given observed gas distribution. The system improves significantly over previous systems, including Gaussian modeling and/or numerical simulation systems, by providing physically accurate, high-resolution forward modeling data inexpensively, thereby enabling detailed location of gas leaks. During operation, the system configures an aerosol source at a first location to emit a gaseous aerosol. The system then configures a laser source to illuminate the aerosol with a laser sheet. The system may then obtain an image of a reflection of the laser sheet from the aerosol. The system may then analyze the image to quantify a three-dimensional concentration distribution of the aerosol. The system may then estimate, based on solving an inverse problem and an observed second gas concentration, a second location of a second gas source.

Overall Process Flow

FIG. 1 illustrates an exemplary overall process flow 100 for estimating a location of a gas leak, according to embodiments of the present invention. As shown in FIG. 1, process flow 100 may apply various forward modeling techniques, such as: an analog or scale model 102; a forward simulation technique 104 like Large Eddy Simulation (LES), Detached Eddy Simulation, or Direct Numerical Simulation, which may be based on the Navier-Stokes equation; or Gaussian modeling 106. The system may apply such techniques to train models and machine learning 108 in order to relate input conditions (e.g., gas source location, wind velocity, topology of terrain and/or well-pad equipment) to a gas concentration distribution. The system can then use models and machine learning 108 to solve an inverse problem 110 relating gas leak characteristics to a gas leak location and/or leak flux quantification. Using the solved inverse problem 110, the system may then process observed gas leak characteristics such as sensor locations, measured gas concentration signal readings, terrain topology, and wind speed and direction, to estimate source coordinates 112 and/or mass flux rate of a gas leak.

Specifically, the disclosed system and methods can utilize an analog or scaled-down experimental model system 102 of a well-head to generate realistic forward data for the development and validation of leak localization algorithms 108. Using dynamic scaling through dimensionless groups, model equipment, such as a small simulated well-head, may be created and instrumented. The system can then subject the model well-head to controlled, external air flow, such as in a wind tunnel. In this way, the disclosed system and methods can measure gas concentration in an analog or model system 102 with similar flow features to the desired actual system, e.g. a functioning well-head.

Thus, physical accuracy is guaranteed in such model systems 102, with the challenge instead shifted towards creating realistic wind and ambient conditions. In order to do so, the system may employ a wind tunnel (e.g., a 4 ft×2 ft wind tunnel at NASA Ames). Wind tunnels are used to visualize fluid flow, particularly wind flow around vehicles and aircraft. Smoke or other aerosol tracers may be used to visualize the path a fluid takes as it passes an object being tested. The system can visualize the fluid's flow in one or more planes as it passes the object. To do so, the system creates smoke upstream, and either disburses the smoke or aerosol over the flow field, or flows the smoke or aerosol as a tracer. The system may then direct a laser sheet through one or more planes of interest, such that the laser light scatters off of the smoke or aerosol, creating a 2D visualization of the fluid flow.

An important domain of the disclosed system is its use for locating leaks in natural gas well-pads. Unlike airplanes, well-pads are situated near ground level, and are therefore usually within the atmospheric boundary layer, or near its edge. In this domain, the wind tunnel simulations are similar to those used to investigate wind flow around bridges and buildings or the flow around moving vehicles. In particular, near the ground, bluff bodies, ground roughness, etc., can engender turbulent flow conditions. In some embodiments, to create an artificial atmospheric boundary layer within a wind tunnel, the test section may be placed behind a long fetch with roughness generators leading to a working section inlet with large spires or wire grids.

System Architecture

FIG. 2 presents a block diagram illustrating an exemplary gas source location estimating system utilizing the gas concentration measurement method, according to embodiments of the present invention. A gas source location estimating system 200 may distribute image or model data and measure gas concentration, according to embodiments, in parallel with multiple processors. In standard systems, system 200 would require forward simulation such as Large Eddy Simulation (LES), Detached Eddy Simulation, or Direct Numerical Simulation. Using the methods disclosed herein, system 200 instead provides high quality forward modeling data much more inexpensively than previous systems.

Gas source location estimating system 200 may include a gas concentration measurement module 202 installed on a storage device 204 coupled to a server 206. Note that various implementations of the present invention may include any number of computers, servers, and storage devices. In various implementations, gas concentration measurement module 202 may include an aerosol source configuring module or other components of gas source location estimating system 200 to perform the techniques described herein. System 200 may receive data describing images and/or models, and store such data in storage device 204. System 200 may read the code for gas concentration measurement module 202 and the data for images and/or models 208 from storage device 204. System 200 may distribute images and/or models data, and assign them to processors, such as processors 210A-210H, which operate on the assigned metric and/or models. System 200 may also include laser source 212, camera 214, and aerosol source 216, which may be coupled directly or indirectly (e.g., via a computer network) to server 206.

Exemplary Measurement Setup

Figure 3:
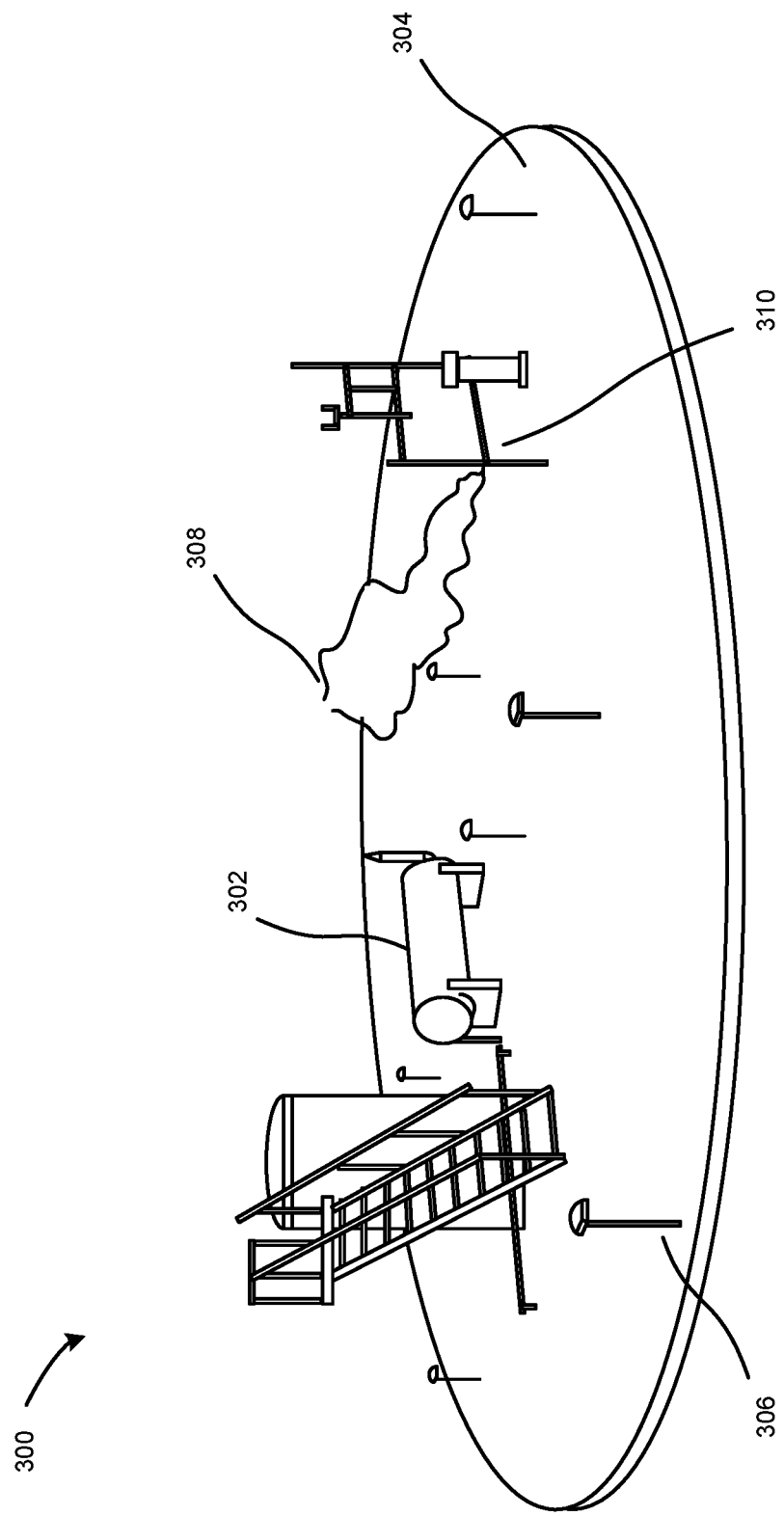

FIG. 3 illustrates an exemplary gas concentration measurement setup 300, according to embodiments of the present invention. To simulate a well-pad, a model with scale components 302 (for example, a small simulated well-head at 1:15 scale) may be fabricated. In some embodiments, model equipment 302 can be created and instrumented via dynamic scaling through dimensionless groups. As shown in FIG. 3, components 302 may be mounted on a rotatable turn table 304 in the test section of a wind tunnel. Turn table 304 allows model components 302 to be rotated to different orientations within the tunnel, thereby simulating different wind directions and conditions.

In some embodiments, measurement setup 300 includes fiduciary points marked by pins or markers 306. Markers 306 may appear as bright points in the subsequent laser reflection image. The system can use these fiduciary points to perform perspective correction while analyzing the image.

In some embodiments, setup 300 includes an aerosol source such as 216, configured to emit a plume 308 of a gaseous aerosol light scatterer, such as vaporized mineral oil. For example, several holes (e.g., three holes) may be drilled in each of well-pad components 302 to emit the aerosol, in order to simulate a gas leak. The system can control the aerosol's buoyancy by varying the composition of a carrier gas used; for example, Nitrogen (i.e., $N_2$), or combinations of Nitrogen and Helium can simulate most gas buoyancies found in practical conditions. In some embodiments, the system configures a particular component 310 from among a plurality of aerosol sources located at predetermined locations (e.g., holes drilled in the different well-pad components) to emit gaseous plume 308. The system may configure component 310 as the selected aerosol source by sending a command (e.g., an electronic command) directly to the equipment 302, or indirectly, e.g., through a computer network.

Method for Measuring a Gas Concentration Distribution

FIG. 4 presents a block diagram illustrating a method for measuring a gas concentration distribution, according to embodiments of the present invention. During operation, the system configures an aerosol source at a first location to emit a gaseous aerosol (operation 402). The system can select a particular aerosol source (e.g., component 310, as illustrated in FIG. 3) from which to emit the aerosol.

The selected aerosol source can be located within a wind tunnel or a turbulent wind tunnel. The system can configure a turn table 304, housing the well-pad components 302 and the selected aerosol source 310, to orient the aerosol source within the wind tunnel. This allows the system to select a relative wind direction or positioning for a given reflection image. Typically, the system configures a camera to take multiple images at different turn table orientations, representing leaks with different wind conditions. The system may select the aerosol source and/or configure the turn table and camera by sending commands. The system may also send commands to configure the buoyancy of the aerosol gas, such as vaporized mineral oil, by adjusting the composition of carrier gas used.

The system then configures a laser source to illuminate the gaseous aerosol with a laser sheet (operation 404). In some embodiments, the laser source may produce green laser light. The laser sheet may scan in a horizontal plane, and may scan upstream of the wind flow direction. The system may use a laser line generator lens to fan out the Gaussian beam into a line of nearly uniform intensity, expanding along the transverse axis at a known rate corresponding to an angle, e.g. 30°. The system may configure one or more laser sources to illuminate the aerosol with multiple laser sheets at different heights and/or orientations. In this way, the system images multiple planes intersecting the gaseous aerosol's volumetric distribution.

The system then obtains, from a camera, an image of a reflection of the laser sheet from a plurality of particles of the gaseous aerosol (operation 406). In some embodiments, the system may obtain a plurality of images from a plurality of laser sheets at different heights and/or orientations. The plurality of images can include images taken with the turn table rotated in order to simulate different relative wind directions, positioning, and/or conditions. The camera may be situated above the measurement setup and at an angle to capture most of the length of the wind tunnel sample area, and to take advantage of the stronger back-scattering signal of the laser. Alternatively a camera with a wide angle lens may be used to image the gaseous flow from directly above. In some embodiments, the system corrects the distortion of the lens. The system may image both with and without a smoke or gaseous aerosol plume, in order to suppress background artifacts through subtraction. The system may repeat this data collection for multiple rotations of the turn-table (to simulate different wind directions on the well-pad), multiple choices of aerosol source (to simulate different leak locations), and multiple heights from the surface (by changing the height of the laser sheet).

The system then analyzes the image to quantify a three-dimensional concentration distribution of the gaseous aerosol associated with the first location (operation 408). In some embodiments, the system analyzes the plurality of images taken under different conditions to quantify the three-dimensional concentration distribution of the gaseous aerosol.

Image Analysis and Gas Concentration Measurement

Figure 5A:
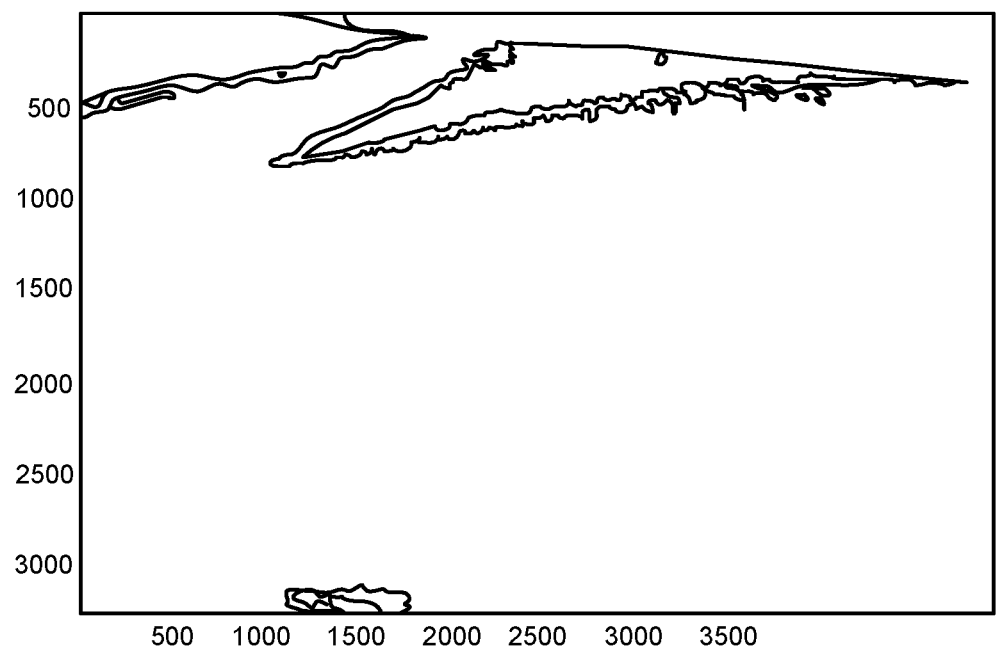

Image analysis 408 is an important element of the disclosed system and methods, as the system can quantify the aerosol concentration distribution with the aid of such analysis. In some embodiments, while analyzing the image, the system removes artifacts from the image. FIG. 5A illustrates an exemplary gaseous aerosol concentration image analyzed by background removal, in accordance with embodiments of the present invention. The system may remove artifacts by differencing an artifact image taken without smoke or gaseous aerosol (i.e., with the aerosol source configured not to emit), from the image with reflection of the laser from the aerosol.

In order to remove artifacts, the system can suppress out-of-plane aerosol signatures of the laser sheet by correlating red, green, and blue (RGB, i.e. the primary colors of light) values for a respective pixel within the image. Specifically, the system may discard pixels that have a correlation between R, G, and B channels, so that only an image of the monochromatic scattered laser light remains. For example, the system may keep green scattered light originating from a green laser sheet, while discarding pixels clearly not corresponding to primary colors. As there may be overlap between both signals, the system may make use of a threshold value chosen to compromise between removal of artifacts and the removal of useful aerosol reflection signal.

Figure 5B:
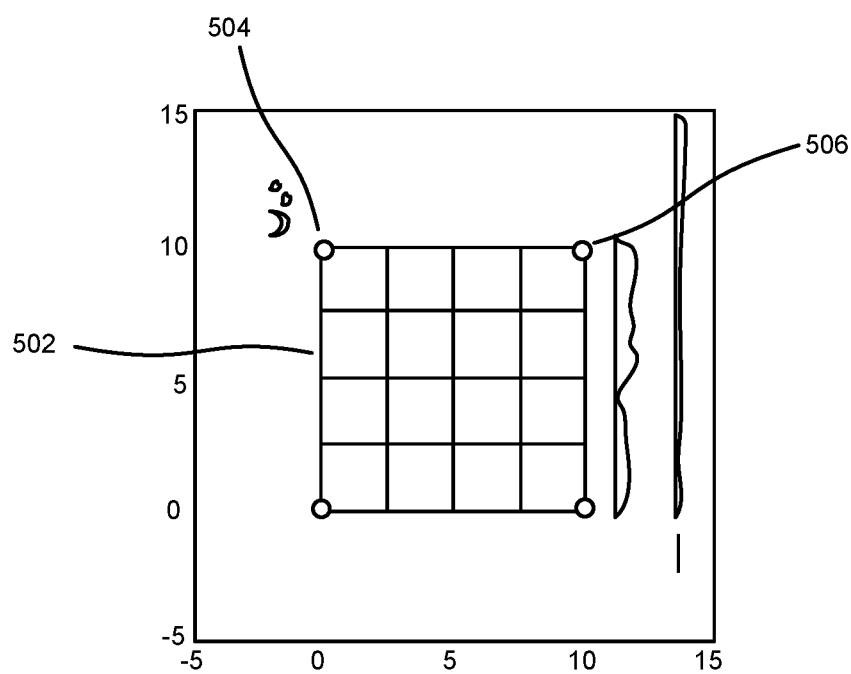

After removing the background, the system may correct for the camera's placement by performing a perspective transformation on the image. In some embodiments, the system calibrates a spatial scale of the image by placing a set of fiduciary points in the measurement setup (e.g., pins or markers such as 306) at known fiduciary locations. FIG. 5B illustrates exemplary fiduciary points used to correct perspective in the image of FIG. 5A, in accordance with embodiments of the present invention. For example, pins or markers may be placed on a 10 inch×10 inch square grid 502, and appear as bright spots, such as 504 and 506, in the image and during subsequent image analysis.

Figure 5C:
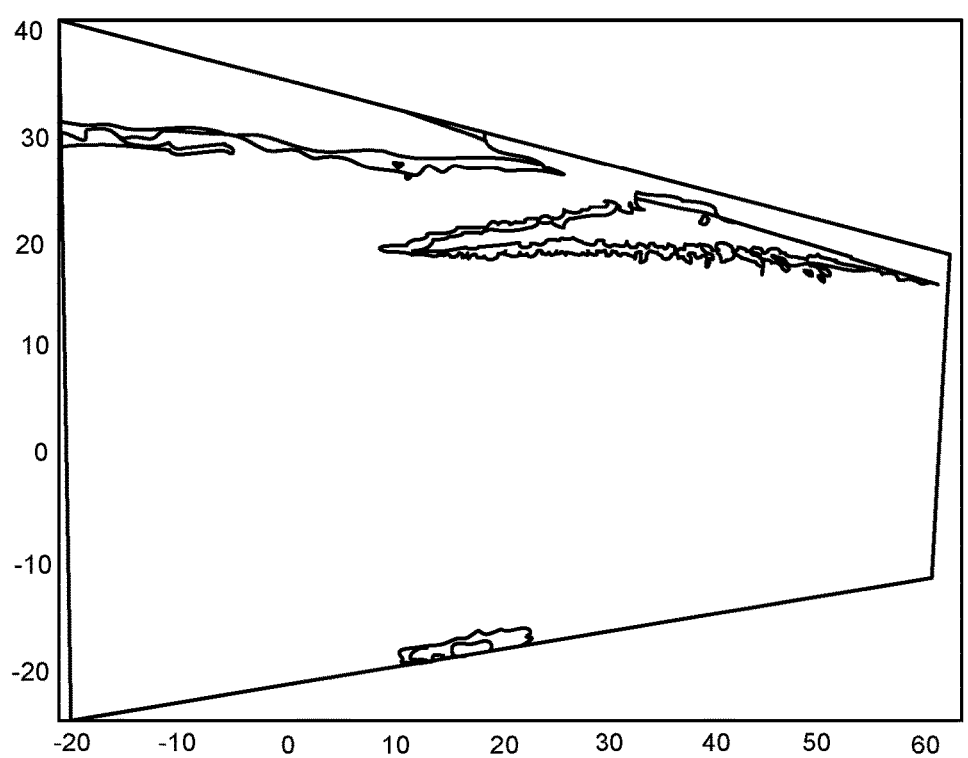

Calibrating the spatial scale can further involve calculating a transformation matrix to correct the positions of spots 504 and 506 onto the known grid 502. By applying the same transformation matrix, the system can then correct the perspective of the image as a whole. In some embodiments, the system may also use permanent fiduciaries on the wind-tunnel floor to calibrate relative distances from the transformation to an absolute scale, which can have an origin in the center of the well-pad. FIG. 5C illustrates the exemplary gaseous aerosol concentration image of FIG. 5A, analyzed by both background removal and perspective correction, in accordance with embodiments of the present invention.

When analyzing the image, the system can also perform normalization for intensity change of the laser due to fanning the laser beam with a line generator lens, in order to expand it into a sheet. The system may also perform normalization against intensity fluctuations along the length of the laser line due to imperfections within the line generator, or the laser beam quality itself. Additionally, because in many circumstances, the gaseous plume is optically thick, the system may correct for laser attenuation due to scattering off the mineral oil or other aerosol. Because multiple images are taken with different rotations of the turn table, the system may also rotate the image such that the leak source is held fixed at one location while the wind direction effectively varies. Note that both the perspective correction and image rotation analyses can result in pixel locations not lying on a uniform grid, thus the system may also resample the pixels to lie on a grid with uniform spacing.

As part of the image analysis, the system can also isolate a plume of the gaseous aerosol by analyzing connectedness of shapes in the image. To do so, the system extracts a bounding square representing the well-pad, and isolates the plume segment of the image. The system may first isolate the plume segment from experimental artifacts by converting all nonzero pixel values (or those above a threshold value) to 1, that is, binarizing the image. While the aerosol plume is a large connected shape within the image, light scattering artifacts are expected to be smaller in volume, and disconnected from the larger plume. Thus, the system may remove all objects in the binarized image that have fewer than a selected threshold number of pixels within a 4-connected neighborhood. The system may then create a connected image using the remaining plume data. Finally, the system can use the coordinates associated with the remaining binary image to reconstruct the plume, using the plume's original concentration values (i.e., those prior to binarizing).

Applying the disclosed methods to multiple experimental scenarios (i.e., choices of leak location, wind direction, and wind speed), the system can build three-dimensional concentration clouds representing 360° wind directions for all leak locations. Once these 3D concentration clouds are created, the system can slice the data along different dimensions (e.g., time or scenarios). The system may also merge data as needed to train machine learning algorithms.

Figure 6:
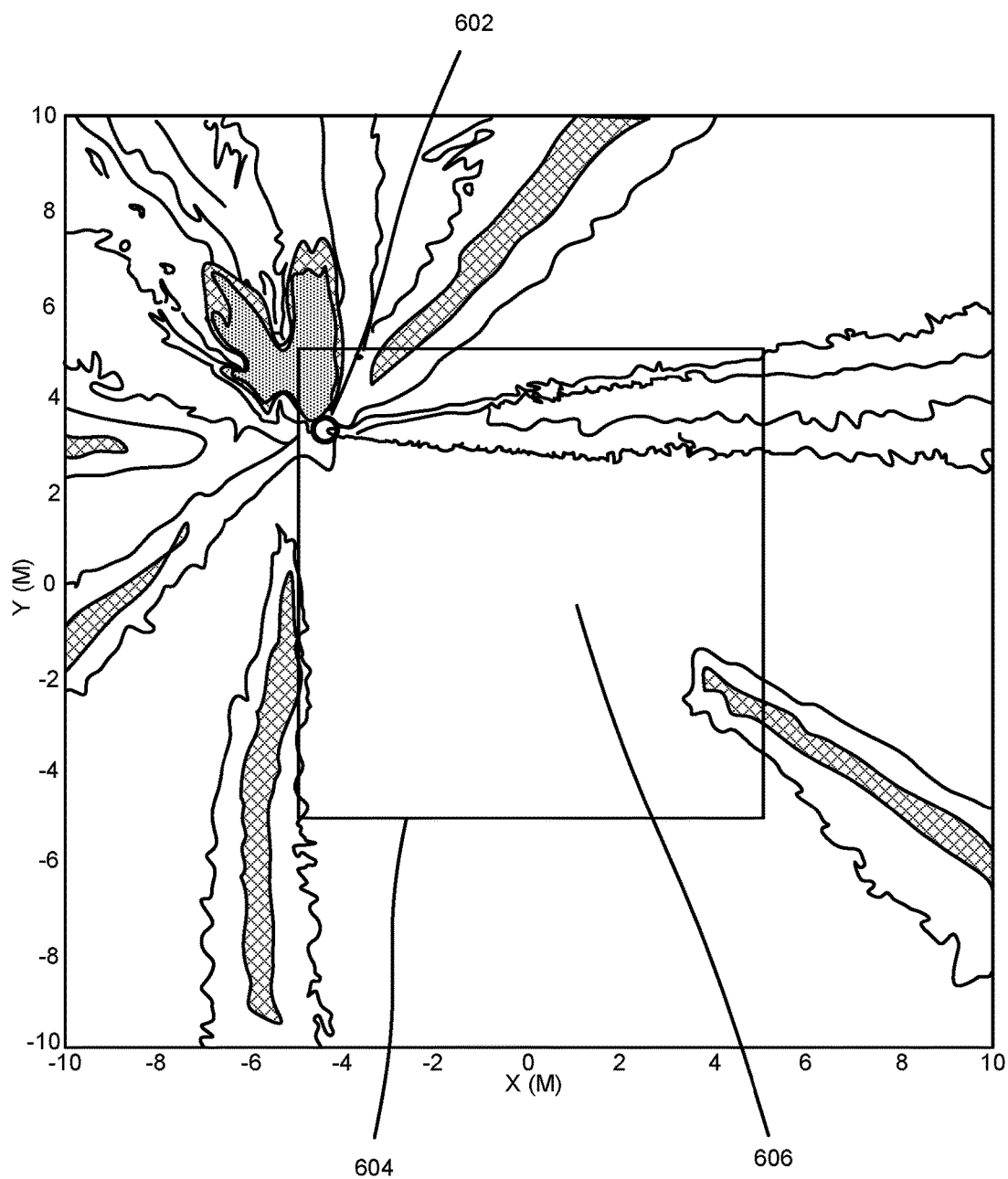

FIG. 6 illustrates an exemplary heat map showing gaseous aerosol plume intensity, in accordance with embodiments of the present invention. For example, the plumes shown in FIG. 6 correspond to a leak source 602 placed at ground level near the Christmas tree standpipe 310, illuminated by a horizontal laser sheet one inch above the ground plane (corresponding to 15" at 1:15 scale). FIG. 6 illustrates an aggregation of scenarios having wind flow rotated at 45° increments relative to the well-pad 604.

Note that the laser-illuminated plume data may have laser shadow regions such as 606, as bluff bodies in the well-pad may block the reflected laser light. This can introduce zones of uncertainty during the leak localization analysis. However, the system can remove such uncertainty by adding a second laser sheet originating from another direction.

After analyzing the image, the system may then solve, based on the three-dimensional concentration distribution and the location of the aerosol source (or the multiple locations and/or other experimental scenarios), an inverse problem (operation 410). The inverse problem may refer to estimating a location of a gas leak based on an observed gas concentration and known wind conditions (i.e., speed and direction) and terrain topology. In some embodiments, the system may train machine learning algorithms to solve the inverse problem, based on the measured three-dimensional concentration distribution and the location of the aerosol source (or the multiple locations, or other experimental scenarios). The system then estimates, based on the solved inverse problem and an observed second gas concentration, a second location of a second gas source (operation 412).

Exemplary Apparatus

Figure 7:
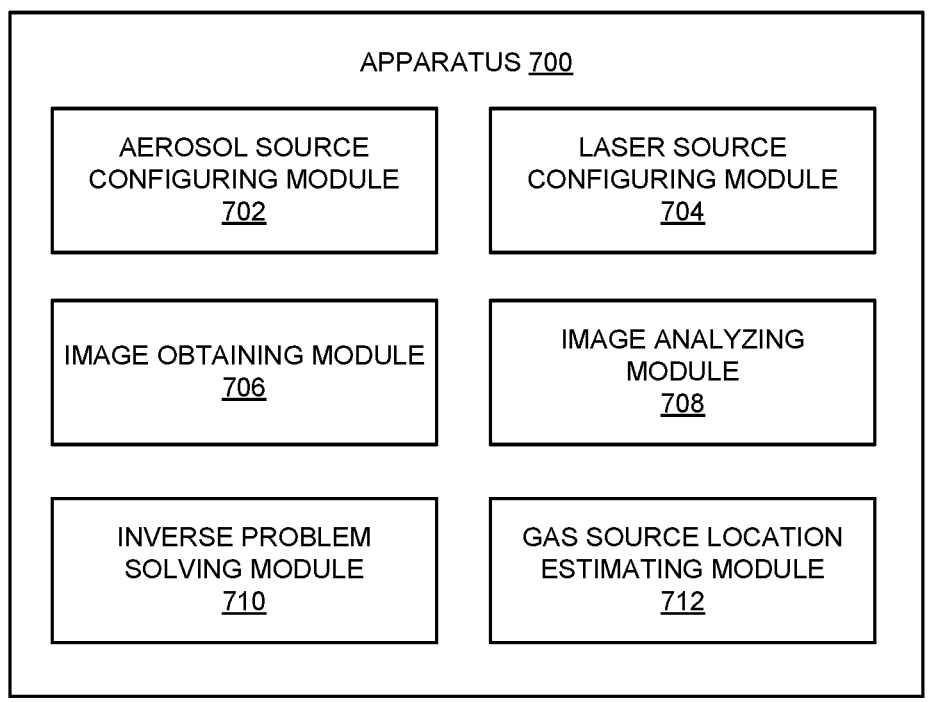

FIG. 7 presents a block diagram illustrating an exemplary apparatus 700 for gas concentration measurement, in accordance with embodiments of the present invention. Apparatus 700 can comprise a plurality of modules which may communicate with one another via a wired or wireless communication channel. Apparatus 700 may be realized using one or more integrated circuits, and may include fewer or more modules than those shown in FIG. 7. Further, apparatus 700 may be integrated in a computer system, or realized as a separate device which is capable of communicating with other computer systems and/or devices. Specifically, apparatus 700 can comprise an aerosol source configuring module 702, a laser source configuring module 704, an image obtaining module 706, an image analyzing module 708, an inverse problem solving module 710, and a gas source location estimating module 712. Note that apparatus 700 may also include additional modules not depicted in FIG. 7.

In some embodiments, aerosol source configuring module 702 can configure an aerosol source at a first location to emit a gaseous aerosol. Laser source configuring module 704 may configure a laser source to illuminate the gaseous aerosol with a laser sheet. Image obtaining module 706 may obtain an image of a reflection of the laser sheet from a camera. Image analyzing module 708 may analyze the image to quantify a three-dimensional concentration distribution of the gaseous aerosol. Inverse problem solving module 710 may solve an inverse problem based on the three-dimensional concentration distribution. Gas source location estimating module 712 may estimate a location of a second gas source. Note that gas concentration measurement module 202 illustrated in FIG. 2 may provide any and all functions of the various modules depicted in FIG. 7.

Exemplary System

Figure 8:
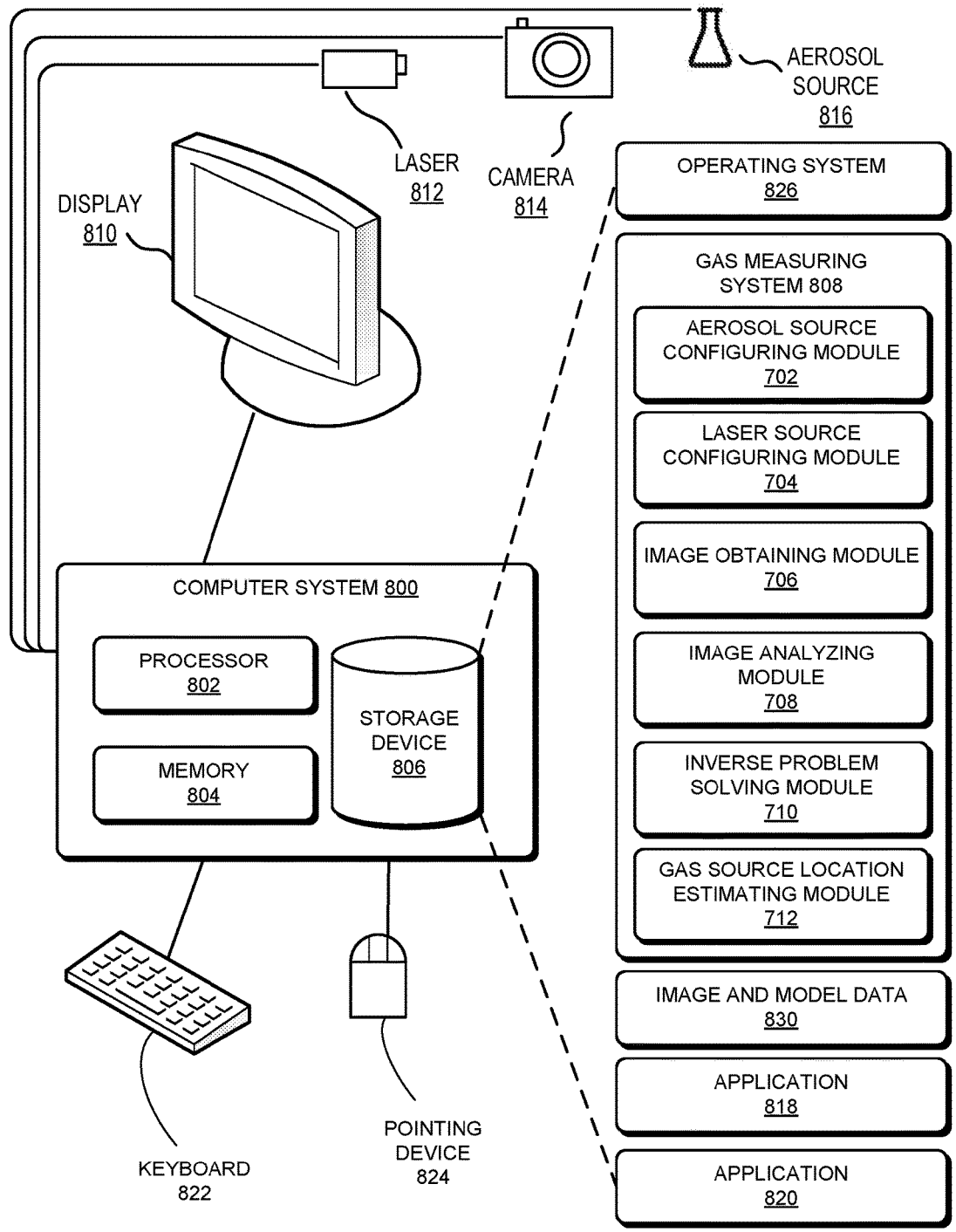

FIG. 8 presents a block diagram illustrating an exemplary computer system for gas concentration measurement, in accordance with embodiments of the present invention. In some embodiments, computer system 800 may be a server. In some embodiments, system 800 includes a processor 802, a memory 804, and a storage device 806. In some embodiments, 802 may include a set of processors. Storage device 806 may store a number of applications, such as applications 818 and 820, which may make use of gas concentration measurement according to embodiments of the present invention, and operating system 826. Storage device 806 also stores gas measuring system 808 that may include an aerosol source configuring module 702, a laser source configuring module 704, an image obtaining module 706, an image analyzing module 708, an inverse problem solving module 710, and a gas source location estimating module 712. System 800 and/or image obtaining module 706 may receive or generate image and model data 830 comprising obtained images and/or models of gas concentration, and may copy image and model data to a memory section accessible to gas measuring system 808. During operation, one or more applications, such as gas measuring system 808, are loaded from storage device 806 into memory 804 and then executed by processor set 802. While executing the program, processor set 802 performs the aforementioned functions. System 800 may be coupled to a display 810, a keyboard 822, and a pointing device 824. System 800 may also include or be coupled directly or indirectly (e.g., via a computer network) to laser source 812, camera 814, and aerosol source 816.

In some embodiments, aerosol source configuring module 702 can configure an aerosol source at a first location to emit a gaseous aerosol. Laser source configuring module 704 may configure a laser source to illuminate the gaseous aerosol with a laser sheet. Image obtaining module 706 may obtain an image of a reflection of the laser sheet from a camera. Image analyzing module 708 may analyze the image to quantify a three-dimensional concentration distribution of the gaseous aerosol. Inverse problem solving module 710 may solve an inverse problem based on the three-dimensional concentration distribution. Gas source location estimating module 712 may estimate a location of a second gas source. Note that gas concentration measurement module 202 illustrated in FIG. 2 may provide any and all functions of the various modules depicted in FIG. 8.

The data structures and code described in this detailed description are typically stored on a computer-readable storage medium, which may be any device or medium that can store code and/or data for use by a computer system. The computer-readable storage medium includes, but is not limited to, volatile memory, non-volatile memory, magnetic and optical storage devices such as disk drives, magnetic tape, CDs (compact discs), DVDs (digital versatile discs or digital video discs), or other media capable of storing computer-readable media now known or later developed.

The methods and processes described in the detailed description section can be embodied as code and/or data, which can be stored in a computer-readable storage medium as described above. When a computer system reads and executes the code and/or data stored on the computer-readable storage medium, the computer system performs the methods and processes embodied as data structures and code and stored within the computer-readable storage medium.

Furthermore, methods and processes described herein can be included in hardware modules or apparatus. These modules or apparatus may include, but are not limited to, an application-specific integrated circuit (ASIC) chip, a field-programmable gate array (FPGA), a dedicated or shared processor that executes a particular software module or a piece of code at a particular time, and/or other programmable-logic devices now known or later developed. When the hardware modules or apparatus are activated, they perform the methods and processes included within them.

The foregoing descriptions of various embodiments have been presented only for purposes of illustration and description. They are not intended to be exhaustive or to limit the present invention to the forms disclosed. Accordingly, many modifications and variations will be apparent to practitioners skilled in the art. Additionally, the above disclosure is not intended to limit the present invention.

What is claimed is:

1. A computer-implemented method for measuring a gas concentration distribution, comprising:
   configuring, by a computer system, an aerosol source at a first location to emit a gaseous aerosol;
   configuring, by the computer system, a laser source to illuminate the gaseous aerosol with a laser sheet;
   obtaining, from a camera, an image of a reflection of the laser sheet from a plurality of particles of the gaseous aerosol;
   analyzing the image to quantify a three-dimensional concentration distribution of the gaseous aerosol associated with the first location; and
   solving, directly based on the three-dimensional concentration distribution and the first location, an inverse problem; and
   estimating, based on the solved inverse problem and an observed second gas concentration, a second location of a second gas source.

2. The method of claim 1, wherein the first location of the aerosol source is within a wind tunnel or a turbulent wind tunnel.

3. The method of claim 2, further comprising selecting a relative wind direction by configuring a turn table to rotate the aerosol source within the wind tunnel or turbulent wind tunnel.

4. The method of claim 1, wherein configuring the aerosol source at the first location further comprises selecting the aerosol source from a set of multiple sources located at predetermined locations.

5. The method of claim 1, further comprising:
   configuring the laser source to illuminate the gaseous aerosol with a plurality of laser sheets at different heights and/or orientations;
   obtaining, from the camera, a plurality of images of reflections of the plurality of laser sheets from the gaseous aerosol; and
   analyzing the plurality of images to quantify the three-dimensional concentration distribution of the gaseous aerosol.

6. The method of claim 1, wherein analyzing the image further comprises one or more of:
   correcting for a placement of the camera by a perspective transformation;
   calibrating a spatial scale of the image using a set of fiduciary points at known fiduciary locations;
   removing artifacts from the image by differencing an artifact image, wherein the artifact image is taken with the aerosol source configured not to emit the gaseous aerosol;
   suppressing an aerosol signature originating out of a plane of the laser sheet by correlating a set of red, green, and blue (RGB) values for a respective pixel within the image; and
   isolating a plume of the gaseous aerosol within the image by analyzing connectedness of shapes in the image.

7. The method of claim 1:
   wherein the first location of the aerosol source is in a scale model of a well-pad; and
   wherein the second gas source is a natural gas leak.

8. A non-transitory computer-readable storage medium storing instructions that when executed by a computer cause the computer to perform a method for measuring a gas concentration distribution, the method comprising:
   configuring an aerosol source at a first location to emit a gaseous aerosol;
   configuring a laser source to illuminate the gaseous aerosol with a laser sheet;
   obtaining, from a camera, an image of a reflection of the laser sheet from a plurality of particles of the gaseous aerosol;
   analyzing the image to quantify a three-dimensional concentration distribution of the gaseous aerosol associated with the first location; and
   solving, directly based on the three-dimensional concentration distribution and the first location, an inverse problem; and
   estimating, based on the solved inverse problem and an observed second gas concentration, a second location of a second gas source.

9. The non-transitory computer-readable storage medium of claim 8, wherein the first location of the aerosol source is within a wind tunnel or a turbulent wind tunnel.

10. The non-transitory computer-readable storage medium of claim 9, wherein the method further comprises selecting a relative wind direction by configuring a turn table to rotate the aerosol source within the wind tunnel or turbulent wind tunnel.

11. The non-transitory computer-readable storage medium of claim 10, wherein configuring the aerosol source at the first location further comprises selecting the aerosol source from a set of multiple sources located at predetermined locations.

12. The non-transitory computer-readable storage medium of claim 8, wherein analyzing the image further comprises one or more of:
   correcting for a placement of the camera by a perspective transformation;
   calibrating a spatial scale of the image using a set of fiduciary points at known fiduciary locations;
   removing artifacts from the image by differencing an artifact image, wherein the artifact image is taken with the aerosol source configured not to emit the gaseous aerosol;
   suppressing an aerosol signature originating out of a plane of the laser sheet by correlating a set of red, green, and blue (RGB) values for a respective pixel within the image; and
   isolating a plume of the gaseous aerosol within the image by analyzing connectedness of shapes in the image.

13. The non-transitory computer-readable storage medium of claim 8:
   wherein the first location of the aerosol source is in a scale model of a well-pad; and
   wherein the second gas source is a natural gas leak.

14. A computing system for measuring a gas concentration distribution, the system comprising:
   a set of processors;
   an aerosol source at a first location;
   a laser source;
   a camera; and
   a non-transitory computer-readable medium coupled to the set of processors storing instructions thereon that, when executed by the processors, cause the processors to perform a method for measuring a gas concentration distribution, the method comprising:

configuring the aerosol source to emit a gaseous aerosol;

configuring the laser source to illuminate the gaseous aerosol with a laser sheet;

obtaining, from the camera, an image of a reflection of the laser sheet from a plurality of particles of the gaseous aerosol;

analyzing the image to quantify a three-dimensional concentration distribution of the gaseous aerosol associated with the first location; and solving, directly based on the three-dimensional concentration distribution and the first location, an inverse problem; and estimating, based on the solved inverse problem and an observed second gas concentration, a second location of a second gas source.

15. The computing system of claim 14, wherein the first location of the aerosol source is within a wind tunnel or a turbulent wind tunnel.

16. The computing system of claim 14, wherein the method further comprises selecting a relative wind direction by configuring a turn table to rotate the aerosol source within the wind tunnel or turbulent wind tunnel.

17. The computing system of claim 14:

further comprising a set of multiple aerosol sources located at predetermined locations; and wherein configuring the aerosol source at the first location further comprises selecting the aerosol source from the set of multiple sources.

18. The computing system of claim 14, wherein the method further comprises:

configuring the laser source to illuminate the gaseous aerosol with a plurality of laser sheets at different heights and/or orientations;

obtaining, from the camera, a plurality of images of reflections of the plurality of laser sheets from the gaseous aerosol; and analyzing the plurality of images to quantify the three-dimensional concentration distribution of the gaseous aerosol.

19. The computing system of claim 14, wherein analyzing the image further comprises one or more of:

correcting for a placement of the camera by a perspective transformation;

calibrating a spatial scale of the image using a set of fiduciary points at known fiduciary locations;

removing artifacts from the image by differencing an artifact image, wherein the artifact image is taken with the aerosol source configured not to emit the gaseous aerosol;

suppressing an aerosol signature originating out of a plane of the laser sheet by correlating a set of red, green, and blue (RGB) values for a respective pixel within the image; and isolating a plume of the gaseous aerosol within the image by analyzing connectedness of shapes in the image.

20. The computing system of claim 14:

wherein the first location of the aerosol source is in a scale model of a well-pad; and wherein the second gas source is a natural gas leak.

* * * * *